United States Patent
Li et al.

(10) Patent No.: US 10,539,490 B2
(45) Date of Patent: Jan. 21, 2020

(54) METHOD AND APPARATUS OF ULTRAFAST PARTICLE DYNAMICS MEASUREMENT BASED ON PHOTON ENSEMBLE CORRELATION SPECTROSCOPY

(71) Applicant: ZHEJIANG UNIVERSITY, Hangzhou, Zhejiang (CN)

(72) Inventors: Peng Li, Zhejiang (CN); Pei Li, Zhejiang (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 0 days.

(21) Appl. No.: 15/742,514

(22) PCT Filed: Feb. 8, 2017

(86) PCT No.: PCT/CN2017/073113
§ 371 (c)(1),
(2) Date: Jan. 7, 2018

(87) PCT Pub. No.: WO2018/129775
PCT Pub. Date: Jul. 19, 2018

(65) Prior Publication Data
US 2019/0086314 A1    Mar. 21, 2019

(30) Foreign Application Priority Data
Jan. 13, 2017   (CN) .......................... 2017 1 0028185

(51) Int. Cl.
*G01N 11/02* (2006.01)
*G01N 15/02* (2006.01)
(Continued)

(52) U.S. Cl.
CPC ......... *G01N 15/0211* (2013.01); *G01N 11/02* (2013.01); *G01N 2011/008* (2013.01);
(Continued)

(58) Field of Classification Search
CPC ........... G01N 15/0205; G01N 15/1459; G01N 2015/1497; G01N 30/02; G01N 15/0211;
(Continued)

(56) References Cited

U.S. PATENT DOCUMENTS

2002/0180972 A1* 12/2002 Ansari ............... G01N 15/0211
356/336
2012/0044493 A1* 2/2012 Smart ................ G01N 15/0211
356/336
(Continued)

FOREIGN PATENT DOCUMENTS

CN     106248532     12/2016

*Primary Examiner* — Michael P Stafira (57) ABSTRACT

An apparatus of ultrafast particle dynamics measurement based on photon ensemble correlation spectroscopy include steps of: dispersing a particle sample to be detected; establishing a plurality of sampling volumes, and collecting dynamic scattered light signals in parallel; and constructing sample ensembles based on scattered signals of the sampling volumes, analyzing time correlations between the sample ensembles, and detecting particle dynamic characteristics. A period for a single measurement of particles according to the method can be in the range of several milliseconds to several tens of milliseconds, which is conducive to real-time detection. More accurate and reliable correlation characterization can be obtained by combining the detected complex-valued scattered signals with both amplitude and phase information. Furthermore, the particle detection is able to be spatially resolved, so as to achieve spatially resolved particle dynamic characteristics.

9 Claims, 4 Drawing Sheets

(51) Int. Cl.
*G01N 11/00* (2006.01)
*G01N 15/00* (2006.01)

(52) U.S. Cl.
CPC ............... *G01N 2015/0038* (2013.01); *G01N 2015/0046* (2013.01); *G01N 2015/0053* (2013.01); *G01N 2015/03* (2013.01)

(58) Field of Classification Search
CPC .......... G01N 21/21; G01N 2015/1493; G01N 2015/1486; G01N 21/65; G01N 21/59; G01N 33/483; G01N 15/042; G01N 15/1463; G01N 2015/0294; G01N 21/53; G01N 2015/0065; G01N 2021/4792; G01N 2015/025; G01N 2015/0288; G01N 2021/4707; G01N 2030/324; G01N 21/3581; G01N 21/4795; G01N 21/51; G01N 21/6428; G01N 21/6486; G01N 2201/0683; G01N 2333/4709; G01N 2800/2821; G01N 30/16; G01N 30/24; G01N 30/30; G01N 30/461; G01N 30/466; G01N 30/54; G01N 30/6052; G01N 30/88; G01N 33/44; G01N 33/487; G01N 33/6896; G01N 35/085; G01N 35/1097; G01N 15/0227; G01N 2021/479; G01N 21/47; G01N 21/4738; G01N 21/55; G01N 33/442; G01N 33/49; G01N 11/00; G01N 15/1404; G01N 15/1429; G01N 15/1434; G01N 15/1475; G01N 2015/0053; G01N 2015/0073; G01N 2015/008; G01N 2015/0084; G01N 2015/0216; G01N 2015/03; G01N 2015/1006; G01N 2015/1087; G01N 2015/1479; G01N 2021/513; G01N 2021/8848; G01N 2030/885; G01N 21/0303; G01N 21/636; G01N 21/8806; G01N 21/9501; G01N 2201/061; G01N 2201/12; G01N 2500/10; G01N 27/44721; G01N 33/5008; G01N 33/502; G01N 33/5026; G01N 33/5044; G01N 35/028; G01N 2021/473; G01N 2021/4735; G01N 2021/4769; G01N 2021/653; G01N 2021/656; G01N 21/03; G01N 21/253; G01N 21/35; G01N 21/41; G01N 21/474; G01N 21/49; G01N 21/532; G01N 2201/0636; G01N 2201/0638; G01N 2201/0675; G01N 2203/0094; G01N 33/4833; G01N 33/4905; G01N 33/54346; G01N 33/54373; G01N 33/587; G01N 33/86; G01N 15/00; G01N 15/0255; G01N 15/05; G01N 1/286; G01N 2001/2866; G01N 2015/0222; G01N 2015/0233; G01N 2015/145; G01N 2021/052; G01N 2021/054; G01N 2021/1729; G01N 2021/1787; G01N 2021/3144; G01N 2021/4186; G01N 2021/4704; G01N 2021/4709; G01N 2021/4711; G01N 2030/625; G01N 21/05; G01N 21/11; G01N 21/1702; G01N 21/1717; G01N 21/251; G01N 21/255; G01N 21/31; G01N 21/45; G01N 21/453; G01N 21/4788; G01N 21/6456; G01N 21/78; G01N 21/82; G01N 2201/06113; G01N 2201/068; G01N 2201/08; G01N 27/44708; G01N 27/44782; G01N 27/44791; G01N 29/2418; G01N 30/60; G01N 30/72; G01N 30/74; G01N 33/721; G02B 6/32; G02B 27/2278; G02B 27/2292; G02B 1/002; G02B 21/08; G02B 27/144; G02B 27/145; G02B 27/283; G02B 27/30; G02B 27/48; G02B 5/0242; G02B 5/0268; G02B 5/0284; G01B 11/08; G01B 9/02091; G01B 2290/65; G01B 9/02032; G01B 9/02043; G01B 9/02044; G01B 9/02084; G01B 9/02087; G01B 9/0209; G01J 3/4412; G01J 3/0218; G01J 3/453; G01J 3/44; G01J 3/45

See application file for complete search history.

(56) References Cited

U.S. PATENT DOCUMENTS

| | | | | |
|---|---|---|---|---|
| 2013/0215423 | A1* | 8/2013 | Tochino | G01N 15/0211 356/336 |
| 2014/0336990 | A1* | 11/2014 | Iwai | G01N 15/0211 702/189 |
| 2017/0322133 | A1* | 11/2017 | Trainer | G01J 3/0218 |
| 2018/0070830 | A1* | 3/2018 | Sutin | A61B 6/00 |

* cited by examiner

METHOD AND APPARATUS OF ULTRAFAST PARTICLE DYNAMICS MEASUREMENT BASED ON PHOTON ENSEMBLE CORRELATION SPECTROSCOPY

CROSS REFERENCE OF RELATED APPLICATION

This is a U.S. National Stage under 35 U.S.C. 371 of the International Application PCT/CN2017/073113, filed Feb. 8, 2017, which claims priority under 35 U.S.C. 119(a-d) to CN 200710028185.0, filed Jan. 13, 2017.

BACKGROUND OF THE PRESENT INVENTION

Field of Invention

The present invention relates to a technical field of optical measurement, and more particularly to a method and apparatus of ultrafast particle dynamics measurement based on photon ensemble correlation spectroscopy, which can be used in industrial production and other aspects for detecting size, viscosity and other information of submicron and nanometer particles.

Description of Related Arts

Particles, which are small dispersed substances, are ubiquitous in nature, manufacturing process and human daily life and other aspects in solid, gas or liquid state forms. Information on particles such as size (particle size) and viscosity is closely related to the properties and quality of the material or product, and even has a significant impact on the quality of the environment and human health. Therefore, the accurate and rapid detection and acquisition of particle information are extremely important to closely related industrial production and scientific research.

For submicron and nanometer particles which are less than 1 μm in size, the materials made from such particles have unique properties due to their surface effects and small size effects. For example, submicron and nanometer iron particles are significantly higher in catalytic efficiency than iron particles of general size. In addition, optical properties of submicron and nanometer particulate materials are beyond the ordinary. For instance nanometer semiconductor materials can be used to prepare new solar cells with high photoelectric conversion efficiency.

In general, for the measurement of particle sizes on the order of submicron and nanometers, due to the limitation of the measurement scale, the conventional particle size detection devices primarily include particle size analyzers based on microscopic measurement and ones based on dynamic light scattering. The particle size analyzers based on microscopic measurement use electron microscopy and scanning probe microscopy technology, enabling visualized measurement of submicron and nanometer particle sizes.

For particles in a suspended particle sample that are comparable in wavelength to light, there is a Doppler shift in the frequency of the scattered light of the particle relative to incident light due to the Brownian dynamic. Therefore, the scattered light signals obtained by coherently superposing the respective scattered light fields of the particles show undulating changes over time. Based on the above principle, the conventional particle size analyzer based on dynamic light scattering characterizes the scattered signal changes over time with time correlation function. According to the Stokes-Einstein equation, the decorrelation rate of the time correlation function is related to the particle size and viscosity, so that the method can be used to detect the size or viscosity information of the particle sample. This dynamic light scattering technique is also known as photon correlation spectroscopy (PCS). However, the above-mentioned PCS method is only for single-scattering particle samples, such as low concentration suspensions. Any multi-scattering component can affect the statistical result of the detected scattered signals. For applying the PCS technique to high concentration scattering samples where multi-scattering is included, photon cross correlation spectroscopy (PCCS) has emerged. However, in this method, a sufficient long time span should be ensured in order to obtain accurate time-dependent functions. In addition, the measuring device is more complicated and costly.

In order to generate a time correlation function, it is necessary to statistically analyze the time correlation between a sufficient amount of independent samples from scattered particles. In order to ensure the reliability and accuracy of the statistical results, the samples are required to be independent of each other, and the number of the samples used for statistical correlation calculation should be sufficiently large. In the above technique based on dynamic light scattering, all the independent samples are sampled at a certain time interval in the temporal dimension, namely the so-called time-mode (TM) measurement. To ensure independence between samples, the time interval should be greater than the decorrelation period (usually a few milliseconds) that is characterized in the time correlation function of the particle sample. Therefore, in order to guarantee the reliability and accuracy of the statistical results, the conventional dynamic light scattering measurement requires a long (about several seconds) total measurement time for a single measurement.

SUMMARY OF THE PRESENT INVENTION

For overcoming defects of conventional particle size analyzers based on dynamic light scattering, an object of the present invention is to provide a method and apparatus of ultrafast particle dynamics measurement based on photon ensemble correlation spectroscopy Accordingly, in order to accomplish the above object, the present invention provides:

I. A method of ultrafast particle dynamics measurement based on photon ensemble correlation spectroscopy, comprising steps of:
1) dispersing a particle sample to be detected;
2) establishing a plurality of sampling volumes, and collecting dynamic scattered light signals in parallel; and
3) constructing sample ensembles based on scattered signals of the sampling volumes, analyzing time correlations between the sample ensembles, and detecting particle dynamic characteristics.

Dispersing the particle sample to be detected specifically comprises a step of dispersing a liquid particle sample to be detected with a wet method or dispersing a gas particle sample to be detected with a dry method.

Establishing the sampling volumes and collecting the dynamic scattered light signals in parallel specifically comprise a step of collecting the dynamic scattered light signals with a low coherence interference method, and further comprises steps of reducing multi-scattered components in the scattered signals and retaining single-scattered components by combining a space gate and a coherence gate with low coherence interference. The low coherence interference further comprises time domain low coherence interferometry that changes an optical path of a reference arm by scanning; spectral domain low coherence interferometry for recording spectral interference signals using a spectrometer; and swept-source low coherence interferometry for recording the spectral interference signals using a swept-frequency light source.

During establishing the sampling volumes and collecting the dynamic scattered light signals in parallel, the sampling volumes are distributed in one or more dimensions selected from a group consisting of a spatial dimension, a spectral dimension, an angular dimension and a polarization dimension. The sampling volumes are further established in a temporal dimension when being supported by a particle detection speed, so as to increase independent samples for improving detecting accuracy.

The spatial dimension comprises a depth space along an optical axis direction, and a lateral space perpendicular to the optical axis direction. The depth space along the optical axis direction is formed by the scattered signals in all depth directions obtained in parallel through Fourier domain low coherence interferometry; and the lateral space perpendicular to the optical axis direction is formed by illuminating different space regions with a plurality of detecting light beams.

The spectral dimension is formed by a plurality of detecting light beams of different spectrums in one space region or different space regions; the spectral dimension is specifically formed by a plurality of light sources of the different spectrums for illuminating, or segmenting a single spectrum after using a wide-spectrum light source for illuminating, or both which specifically illuminates with the light sources of the different spectrums and then segments a spectrum.

The angular dimension is formed by a plurality of detecting light beams incident on a same space region or different space regions from different angles, and then using optical path coding, or transverse modulation spectrum segmentation, or detecting with multiple detectors.

For further establishing the sampling volumes in the temporal dimension, a sample ensemble with more samples is formed at any one of current time points by combining samples in the sampling volumes of subsequent time points and the current time points.

During establishing the sampling volumes and collecting the dynamic scattered light signals in parallel, the dynamic scattered light signals are intensity signals, amplitude signals, or complex signals comprising both amplitude information and phase information.

Constructing the sample ensembles based on the scattered signals of the sampling volumes, analyzing the time correlations between the sample ensembles, and detecting the particle dynamic characteristics specifically comprise steps of: defining a time point as an initial time point, calculating the time correlations between the sample ensembles of subsequent time points and the initial time point, and detecting the particle dynamic characteristics according to decay characteristics of ensemble correlations over time.

Detecting the particle dynamic characteristics specifically comprises a step of: obtaining particle size information through correlation calculation when a viscosity is certain; or obtaining viscosity information through the correlation calculation when a particle size is certain.

II. An apparatus of ultrafast particle dynamics measurement based on photon ensemble correlation spectroscopy, comprising:

a particle sample dispersing device, for dispersing a particle sample to be detected into a space;
an optical illuminating and detecting device, for establishing a plurality of sampling volumes, and collecting dynamic scattered light signals in parallel; and
at least one processor, for analyzing scattered signals detected.

The optical illuminating and detecting device comprises a low coherence light source, an interferometer and a detector; or comprises the low coherence light source, the interferometer and a spectroscopy; or comprises a swept-frequency wide-spectrum light source, the interferometer and the detector; and further comprises a scanning device capable of changing a light beam position.

The optical illuminating and detecting device comprises elements selected from a group consisting of: an illuminating device using a plurality of light beams to illuminating different lateral space positions perpendicular to an optical axis direction, and a multi-detector device, for establishing the sampling volumes in a spatial dimension; an illuminating device using the light beams to illuminating a same space position or different space positions with different incidence angles, and the multi-detector, for establishing the sampling volumes in an angular dimension; a single-beam illuminating device formed by a plurality of sub-beams, wherein the sub-beams have different optical path delays and illuminate the same space position or the different space positions with different incidence angles, so as to establish the sampling volumes in the angular dimension and detect the sampling volumes in parallel with optical path coding; and a multi-beam illuminating device with different spectrums, wherein different light beams illuminates the same space position or the different space positions; which is specifically formed by a plurality of light sources of the different spectrums for illuminating, or segmenting a single spectrum after using a wide-spectrum light source for illuminating, or both, for establishing the sampling volumes in a spectral dimension.

Analyzing the scattered signals detected by the processor further comprises constructing the sampling volumes by segmenting a spectrum, an optical path or a transverse scanning modulation spectrum during analyzing the scattered signals detected.

Analyzing the scattered signals detected by the processor further comprises defining a time point as an initial time point, calculating the time correlations between the sample ensembles of subsequent time points and the initial time point, and detecting the particle dynamic characteristics according to decay characteristics of ensemble correlations over time.

Compared with the prior art, the present invention has beneficial effects and advantages as follows.

Combined with low coherence interference and dynamic light scattering technology, the space gate with low coherence interference can effectively restrain multiple scattering, and scattered signal samples from multiple sampling volumes recorded at different time points are used for ensemble analysis and time correlation calculation. Based on decay characteristics, particle size or viscosity information is determined.

Compared with the conventional dynamic light scattering particle sizer which can only obtain one-dimensional light intensity signal for time correlation analysis, the present invention can detect the complex-valued scattered signals from particles in the multi-dimensional space comprising the depth direction, the transverse space perpendicular to the depth, the spectral dimension, the detecting light incident angle dimension and the optical polarization state dimension at different time points, and can combine the amplitude and phase information to obtain a time correlation function of the complex-valued signals. Compared with pure amplitude (or intensity) signal analysis, the present invention increases the reliability and accuracy of statistical calculation of signal correlation with decay over time.

The conventional dynamic light scattering particle sizer which only calculates time autocorrelation function for one-dimensional time-series of scattered signal samples. In this process, independent samples are obtained by sampling in the temporal dimension. In order to ensure the reliability and accuracy of the statistical measurement results, a single measurement requires a long total measurement period (about a few seconds), which increases the time cost. The present invention can adopt dynamic light scattring based sample ensemble measurement, which can obtain sufficient samples of scattered signals in parallel in a multi-dimensional sampling volume including depth space, and the single measurement time can be shortened to several milliseconds. The accuracy and repeatability of the data are sufficient for rapid detection of particle information.

Compared with the conventional dynamic light scattering particle sizer which only detects one-dimensional time-varying light intensity signals, the present invention enables the parallel detection of scattered light signals in two or more dimensions, enabling the measurement of the characteristics of spatially resolved scattered particle samples.

Element reference: 1—dispersing a particle sample; 2—establishing a plurality of sampling volumes, and collecting dynamic scattered light signals in parallel; 3—analyzing scattered signal sample ensembles; 11—light source; 12—beam splitter; 13—reference arm collimator; 14—flat high reflection mirror; 15—sample arm collimator; 16—scanning mirror; 17—objective lens; 18—particle dispersing device; 19—interference signal detecting device; 20—signal processor; 21—polarization controller; 31—low—coherence broadband light source; 32—optical circulator; 33—optical fiber coupler; 34—first optical fiber collimator; 35—focusing lens; 36—flat high reflection mirror; 37—second optical fiber collimator; 38—scanning mirror; 39—objective lens; 40—sample dispersing device; 41—third optical fiber collimator; 42—optical grating; 43—Fourier transformation lens; 44—high—speed line—scan camera; 45—signal processor module and calculation unit; 46—first polarization controller; 47—second polarization controller.

DETAILED DESCRIPTION OF THE PREFERRED EMBODIMENT

The specific embodiment of the present invention will be described in detail below with reference to the accompanying drawings, which form a part hereof. It should be noted that these descriptions and examples are merely exemplary and should not be construed as limiting the scope of the present invention which is defined by the appended claims. Any modifications based on the claims of the present invention are within the protection scope of the present invention.

For easily understanding the embodiment of the present invention, operations are described as a plurality of discrete operations. However, the order of description does not represent the order in which the operations are performed.

This description uses a representation of mathematical variables for the measurement space. This description is for the purpose of promoting discussion only and is not intended to limit the application to the embodiment of the present invention, wherein: z denotes a depth direction, namely a direction along an incident optical axis; t denotes a time index, referring to different time points corresponding to scattered signals measured at a same position.

The basic idea of the present invention is to construct a plurality of sampling volumes to detect and collect the particle dynamic scattered light signals (including amplitude and phase information) in parallel, and construct sample ensembles by scattered signals from the sampling volumes, then analyze and calculate sample ensemble correlation over time as well as detect particle dynamic characteristics.

Figure 1:
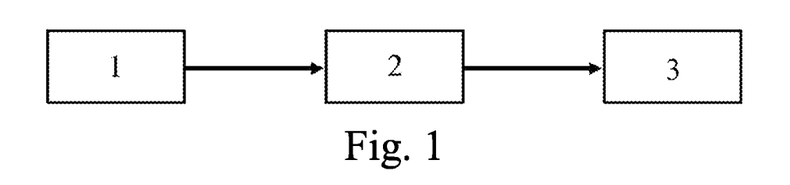
FIG. 1 is a schematic view of a method of the present invention.

FIG. 1 is a schematic view of a method of ultrafast particle dynamics measurement based on photon ensemble correlation spectroscopy of the present invention. A particle dispersing device is used for fully dispersing a particle sample 1 in a certain space, comprising dispersing a liquid phase particle with a wet method or dispersing a gas phase particle with a dry method, so as to prepare space-distributed particle samples to be detected. In a liquid media, it is guaranteed that the dispersing liquid does not dissolve or agglomerate the particles and a refractive index of the liquid is different from that of the particle samples to be detected.

Figure 7:
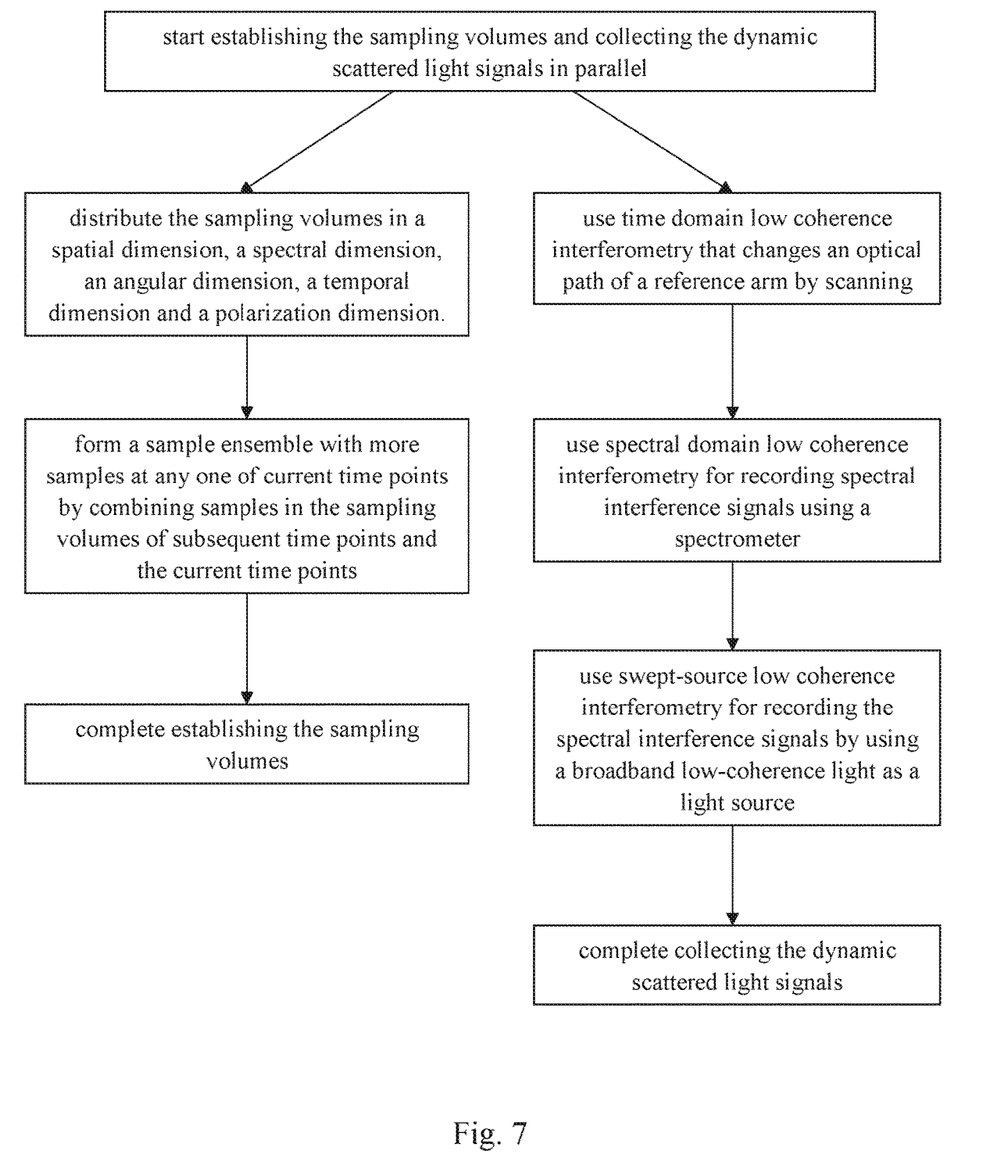
FIG. 7 is a block diagram of establishing the sampling volumes and collecting the dynamic scattered light signals in parallel the present invention.

Establishing a plurality of sampling volumes, and collecting dynamic scattered light signals in parallel 2 (the dynamic scattered light signals are intensity signals, amplitude signals, or complex-valued signals comprising both amplitude information and phase information) is achieved by low coherence interference detection. The space gate with the low coherence interference detection can effectively restrain multiple scattering. Referring to FIG. 7, signal collecting of the low coherence interference is achieved by time domain low coherence interferometry that changes an optical path of a reference arm by scanning; spectrum domain low coherence interferometry for recording spectrum interference signals using a spectrometer; or swept-frequency low coherence interferometry for recording the spectrum interference signals using a swept-frequency light source.

At different time points t, the sampling volumes of particle dynamic scattered signals are collected, and are distributed in one or more dimensions such as space, spectrum, incidence angle, polarization dimensions, providing a variety of sampling volume combinations to form a large sample ensemble; wherein the temporal dimension comprises a depth space along an optical axis direction, and a lateral space perpendicular to the optical axis direction: the sampling volumes of the depth space along the optical axis direction are obtained by the scattered signals in all depth directions obtained in parallel through Fourier domain low coherence interferometry; and the sampling volumes of the lateral space perpendicular to the optical axis direction are obtained by illuminating different space regions with a plurality of detecting light beams.

The sampling volumes of the spectral dimension are obtained respectively using light sources of different spectrums in a same space region; or by segmenting a single wide spectrum, namely segmenting a scattered signal spectrum detected by low coherence interference in the wave number domain at any time point, so as to obtain several independent sub-spectrums and finally obtain multiple independent scattered signal sampling volumes by Fourier transform; or using both methods.

Obtaining a plurality of independent sampling volumes in the angular dimension refers to collecting samples from illumination of detecting light from N angle regions, with a plurality of detecting light beams incident on a same space region or different space regions from different angles; or detecting in different angle regions by different optical path delay, wherein the N angle regions are encoded into M detection range regions, and then detection range is split to generate the sampling volumes of N angles; or independently detecting the scattered signals at different times or spaces, and segmenting according to time or space features, so as to generate the sampling volumes of N different angle regions; or segmenting a transverse modulation spectrum of the collected scattered signals to obtain a plurality of angular encoded sub-modulation spectrums (as disclosed in Chinese application 2016201159236, filed Feb. 5, 2016), and finally generating a plurality of sampling volumes of detecting light angular dimension Obtaining a plurality of independent sampling volumes in the polarization dimension is to provide polarization state modulation of reference light detected by low coherence interference, and coherently extract optical signals which are corresponding to different polarization states of the incident light and are backscattered, so as to get multiple sampling volumes.

Analyzing scattered signal sample ensembles constructed through sampling volumes of scattered signals 3 for detecting particle dynamic characteristics comprises steps of:

defining a time point as an initial time point, calculating the time correlations between the sample ensembles of subsequent time points and the initial time point, and detecting the particle dynamic characteristics according to decay characteristics of ensemble correlations over time; based on Einstein-Stokes equations, obtaining particle size information through correlation calculation when a viscosity is certain; or obtaining viscosity information through the correlation calculation when a particle size is certain. In addition, the process can select independent samples in the temporal dimension. Specifically, in the sample ensemble of the original ensemble analysis, each sample volume at multiple time points subsequent to the subsequent time point is combined with the sampling volumes at observed time points, so as to obtain sample ensembles with more samples, wherein the reliability of the statistical calculation of correlation is increased to improve the detection accuracy. In addition, by changing the space positions of the sampling volumes, such as changing the detection area by scanning, it is possible to detect the particle features at different positions in the space, so as to enable imaging of particle dynamic features.

Figure 2:
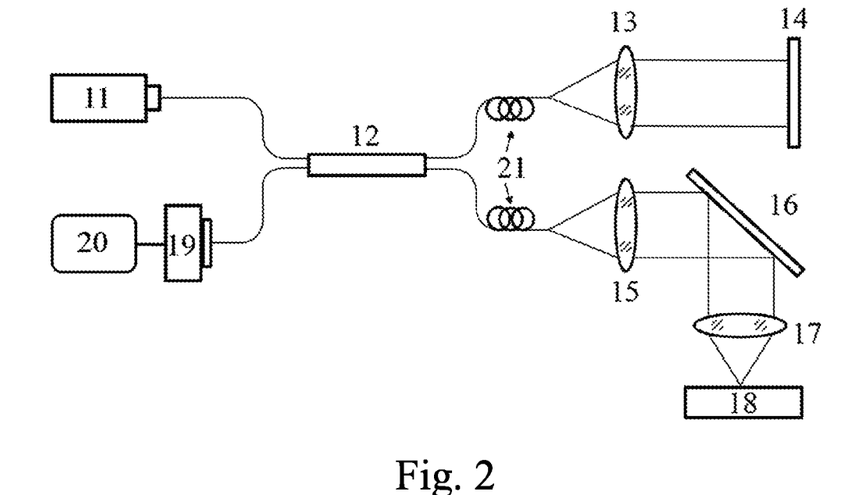
FIG. 2 is a schematic diagram of a device of the present invention.

FIG. 2 is a schematic diagram of an apparatus of ultrafast particle dynamics measurement based on photon ensemble correlation spectroscopy of the present invention. A particle dispersing device 18 is used for fully dispersing a particle sample in a certain space, comprising dispersing a liquid phase particle with a wet method or dispersing a gas phase particle with a dry method, so as to prepare space-distributed particle samples to be detected. An optical illuminating and detecting device, for establishing a plurality of sampling volumes and collecting dynamic scattered light signals in parallel is achieved by low coherence interferometry. A main body of a low coherence interferometry detecting part of the device comprises elements 11-19, 19 and 21, wherein light from a light source 11 is divided into two beams by a beam splitter 12, a first beam enters a reference arm of an interferometer and reaches a flat high reflection mirror 14 through a reference arm collimator 13; a second beam enter a sample arm and is focused on a sample to be detected through a sample arm collimator 15 and optical path reflection. The particle dispersing device 18 is used for dispersing the sample before placing the sample at a focal plane of an objective lens 17 of the sample arm. Light beams respectively reflected by the reference arm and the sample arm generate interference which is detected by an interference signal detecting device 19. For an optical fiber path, a polarization controller is used for adjusting polarization states of the beams, so as to optimize a signal interference effect.

According to different low coherence interference signals, the ultrafast particle dynamics measurement apparatus shown in FIG. 2 comprises devices as follows.

1) a time domain detecting device. The light source 11 adopts broadband low-coherence light, the flat high reflection mirror 14 is movable along an optical axis direction, and the interference signal detecting device 19 is a point detector. The reference arm optical path can be adjusted through moving the flat high reflection mirror 14, the interference signals of the two arms are detected by the interference signal detecting device 19, wherein the scattered signals along a z-axis direction of a certain space depth is detected by low coherence interference, so as to obtain sampling volumes of the depth space dimension.

2) a spectral domain detecting device. The light source 11 adopts the broadband coherent light, the flat high reflection mirror 14 is fixed, and the interference signal detecting device 19 is a spectrometer. The interference spectrum of the interference signals is simultaneously recorded when the interference signals pass through a line-scan camera of the spectrometer. Interference spectrum signals are analyzed by a Fourier analysis method, and scattering information at a z-axis direction of a depth is obtained, so as to obtain the sampling volumes in the depth space dimension.

3) a swept-source detecting device. The light source 11 adopts the broadband low-coherence light, the flat high reflection mirror 14 is fixed, and the interference signal detecting device 19 is the point detector. The point detector asynchronously records low coherence interference spectrum of a swept-frequency light source. The interference spectrum signals are analyzed by the Fourier analysis method, and the scattering information at the z-axis direction of the depth is obtained, so as to obtain the sampling volumes of the depth space dimension.

The above detecting devices can respectively be combined with different detecting method shown in FIG. 1, and use a signal processor 20 for processing the detected scattered signals with methods shown in FIG. 1 (comprising segmenting the spectrum, segmenting the optical path or segmenting the transverse scanning modulation spectrum for obtaining a plurality of sampling volumes, so as to increase independent sample ensembles), for determining viscosity or size information of the particles, so as to image the characteristics of particle dynamics. Different sampling volumes are obtained by different detecting methods with the following implements:

- an illuminating device using a plurality of light beams to illuminating different lateral space positions perpendicular to an optical axis direction, and a multi-detector device, for establishing the sampling volumes in a spatial dimension; wherein multiple devices as shown in FIG. 2 may be used; each detecting light beam reaches different lateral space positions perpendicular to the optical axis direction through the objective lens 17 of the sample arm;
- an illuminating device using the light beams to illuminating a same space position or different space positions with different incidence angles, and the multi-detector, for establishing the sampling volumes in an angular dimension; wherein a single light beam from the polarization controller 21 of the sample arm may be divided into a plurality of beams which are spacely separated, and the beams reach a surface of a sample through the sample arm with different incidence angles for multi-angle detection;
- a single-beam illuminating device formed by a plurality of sub-beams, wherein the sub-beams have different optical path delays and illuminate the same space position or the different space positions with the different incidence angles, so as to establish the sampling volumes in the angular dimension and detect the sampling volumes in parallel with optical path coding, as described in Chinese application 201620115923.6, filed, 2016 Oct. 5;
- a multi-beam illuminating device with different spectrums, wherein different light beams illuminates the same space position or the different space positions; which is specifically formed by a plurality of light sources of the different spectrums for illuminating, or segmenting a single spectrum after using a wide-spectrum light source for illuminating, or both, for establishing the sampling volumes in a spectral dimension; wherein the light source may comprises a plurality of light sources which different spectrum distribution; light emitted enters an end of the beam splitter 12 after being coupled, then enters a main volume of the interference detecting device, and the detecting light beams reach a same position of the sample. Finally, corresponding optical interference signals of different spectrums are received by different interference signal detecting device 19.

In the embodiment of the present invention:

in the following detailed description, reference is made to the drawings which form a part hereof and are shown by way of example embodiments in which the invention may be practiced. It should be understood that other embodiments may be utilized, and structural or logical changes may be made without departing from the scope of the present invention. Thus, the following detailed description is not to be limiting, and the scope of the embodiment in accordance with the present invention is defined by the appended claims and their equivalents.

According to the embodiment, the method and apparatus of ultrafast particle dynamics measurement based on photon ensemble correlation spectroscopy are implemented by a series of processes, comprising reducing multi-scattered components in the scattered signals and retaining single-scattered components by combining a space gate and a coherence gate with low coherence interference, then determining particle size and viscosity information according to ensemble correlation features over time of scattered complex-valued signals in multiple sampling volumes.

Figure 3:
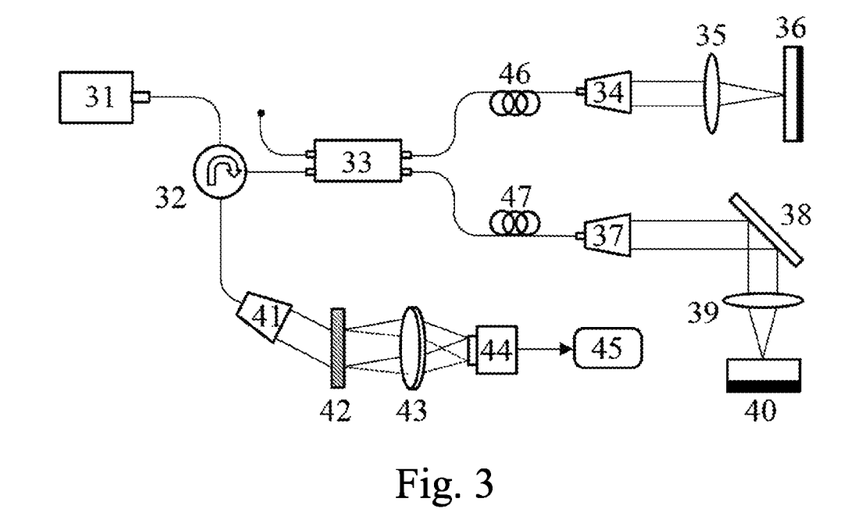
FIG. 3 is a schematic diagram of an embodiment of the present invention.

FIG. 3 is a schematic diagram of the embodiment of the present invention. An apparatus of ultrafast particle dynamics measurement based on photon ensemble correlation spectroscopy comprises a low-coherent broadband light source 31, an optical circulator 32, an optical fiber coupler 33 with a splitting ratio of 50:50, a first polarization controller 46, a first optical fiber collimator 3, a focusing lens 35, a flat high reflection mirror 36, a second polarization controller 47, a second optical fiber collimator 37, a scanning mirror 38, an objective lens 39, a sample dispersing device 40, a third optical fiber collimator 41, an optical grating 42, a Fourier transformation lens 43, a high-speed line-scan camera 44, and a signal processor module and calculation unit 45; wherein the low coherent broadband light source 31 adopts a superluminescent diode with a central wavelength of 1325 nm and a full width at half maximum of 100 nm, the objective 39 is an achromatic doublet lens with a focal length of 33 mm, the high-speed line-scan camera 44 is a line-scan camera with 2048 pixels; wherein light from the low coherent broadband light source 31 of the present invention enters the optical fiber coupler 33 with the splitting ratio of 50:50 through the optical circulator, and is divided into two beams by the optical fiber coupler 33; a first beam reaches the first optical fiber collimator 34 in a reference arm through the first polarization controller 46, and reaches the flat high reflection mirror 36 after being collimated and focused; a second beam reaches the second optical fiber collimator 37 in a sample arm through the second polarization controller 47, and reaches a sample to be detected after being collimated, reflected and focused. The sample dispersing device 40 fully disperses polystyrene microsphere particles in a distilled water solution with a wet method for obtaining the sample to be detected. The scanning mirror 38 in the sample arm is fixed, so that the low coherence interferometer can detect the scattered signals in the depth direction at the same position of the sample space at different times in parallel. At the same time, the optical path in the sample arm conducts the light beam through a single-mode optical fiber, which provides space filtering for the light scattered back from the sample to be tested, namely effectively reducing the multiple scattered components in the scattered signals. The light reflected by the flat high mirror 36 in the reference arm and back-scattered light of the sample in the sample arm interfere at the optical fiber coupler 33, and interference light is detected by a spectrometer (comprising the devices 41-44) and recorded. The signal processor module and calculation unit 45 collects and analyzes the signals.

Any detected scattered signal can be expressed as a 3-dimensional data set after pre-treatment, i.e. $D(z_i, t)$, wherein $z_i$ ($t=1:N$) refers to the depth direction corresponding to all scattering information in a certain depth space of the sample, where N denotes the total number of signal sample elements, t denotes different time points of repeatedly detection at a same position and D denotes a complex-valued array representing a complex-valued scattered signal that contains both phase and amplitude information.

For sample ensembles analysis: a time point $t_n$ is defined as an initial time point, and corresponding complex-valued scattered signals (the sample ensembles) of a whole depth space are represented as $D(z_i,t_n)$, and correlation of complex-valued scattered signals corresponding to subsequent time points ($t_n+\Delta t$, $t_n+2\Delta t$, $t_n+3\Delta t$, ..., $t_n$ to $+\alpha\Delta t$, wherein $\Delta t$ is an interval between signal recording, $\alpha$ is a number of the time points) is respectively calculated with $D(z_i,t_n)$, namely:

$$G(\tau) = \lim_{N\to\infty} \frac{1}{N}\left|\sum_{i=1}^{N} D(z_i, 0)D*(z_i, \tau)\right|, \quad (1)$$

wherein $\tau$ is time delay corresponding to different time points after the initial time point $t_n$. As a result, a curve of correlation G of the sample ensemble over time is obtained. Theoretically, changes of the correlation over time obeys Lorentz exponential decay distribution:

$$G(\tau) \sim \exp(-2\tau/\tau_c) = \exp(-D_T q^2 \tau), \quad (2)$$

wherein $\tau_n$ represents a decorrelation period; $D_T q^2$ is a decay coefficient, characterizing a decorrelation rate of a time-dependent function; $D_T$ represents a diffusion coefficient, which can be derived from the Stokes-Einstein equation:

$$D_T = k_B T/3\times\eta d, \quad (3)$$

wherein $k_R$ represents a Boltzmann constant; T represents an absolute environment temperature during detecting; $\eta$ represents a viscosity of the particle sample; and d represents a diameter of the sample to be detected. A scattering vector q can be determined by the following formula:

$$q = 4\pi n \sin(\theta/2)/\lambda, \quad (4)$$

wherein n represents a medium refractive index; $\theta$ represents a scattering angle; and $\lambda$ represents a central wavelength of a detecting light beam in vacuum. For small particles, the time-dependent decay of scattered signals is fast and a delay time is shorter. For large-size particles, the time-dependent decay of the scattered signals is slow and the delay time is longer. By measuring the time-dependent functions of particle samples of different sizes, a particle size can be determined when a viscosity is certain, or sample viscosity information can be determined when the particle size is certain.

According to the present invention, the particle samples of different sizes (with diameters of $\Phi 44$ nm, $\Phi 100$ nm, $\Phi 1200$ nm, and with a same volume concentration of 10 vol %) are detected by the device as shown in FIG. 3. After being fully dispersed in a liquid phase, the particle sample to be detected is placed at a detecting position of the apparatus. Generally, for a particle sample with a certain size, a theoretic value the decorrelation period is calculated with the above ensemble correlation as follow: a standard diameter d of the particle sample is known; according to formulas 2-4, the theoretic value of the decorrelation period $\tau_n$ is obtained with conditions of $k_R=1.38\times10^{-23}$ J·K$^{-1}$, T=297.15K, $\eta=9.142\times10^{-8}$ N·s·cm$^{-2}$, T=297.15K and $\theta=\pi$ rad. Actually, the correlation of the particles over time can be fully characterized within one decorrelation period. Therefore, a data collecting period can be reduced to one decorrelation period. Theoretically, the decorrelation periods of 44 nm, 100 nm and 200 nm particles are 1.17 ms, 2.65 ms and 5.30 ms, respectively. As a result, in actual detection of these three kinds of particles, complex-valued backscattered signals in depth sample space from 90, 204 and 408 time points (with a time interval of 13 μs) are recorded in single detection, respectively. Single detection period is consistent with the decorrelation period, and the detection is repeated 10 times to obtain mean and standard deviation.

Figure 4:
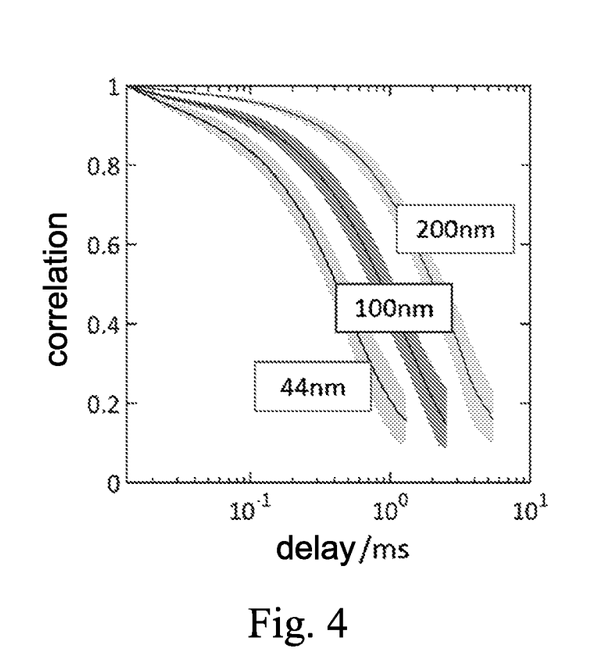
FIG. 4 illustrates a result of ensemble correlation of different particles changing over time according to the embodiment of the present invention.

A total of 200 spatial positions along the depth direction are selected, which contain effective complex-valued signals from scattered particles. For single detection data of any particle sample (such as the 44 nm particle), the scattered complex signal (200 depth space positions) at the first time point is selected as a reference, and correlation calculation is provided respectively with all scattered signals within a same depth range at No. 1, 2, ... 90 time points. The above experimental process is repeated 10 times for repeated detection, and then obtaining the mean and standard deviation. The relationship curve of particle correlation over time in different samples is finally obtained. FIG. 4 illustrates the correlation curve, wherein a curve portion refers to average values, and filled areas around the curve portions represent the standard deviation. An abscissa indicates a delay time in logarithmic coordinates and an ordinate indicates the correlation. The detected time-dependent function is fitted by exponential distribution using a least square method, and the diameters of the particles are calculated by inversion. The diameters of the three different particles are 45.82±2.12 nm, 97.75±1.88 nm and 209.07±1.82 nm. Detection results are consistent with the standard diameters.

Figure 5:
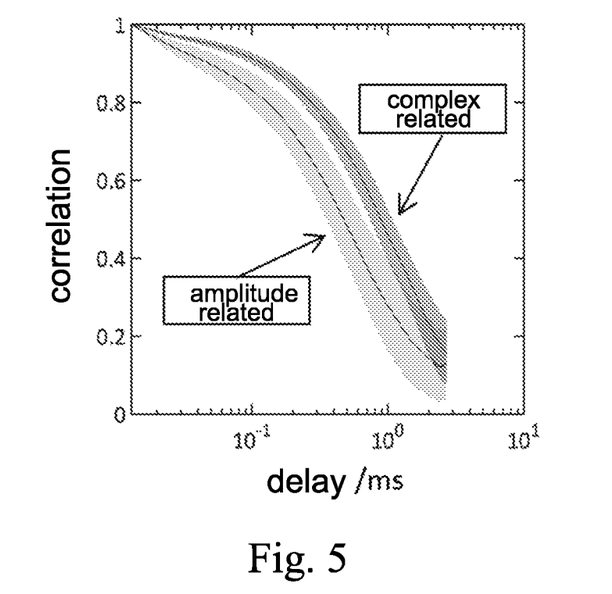
FIG. 5 illustrates ensemble correlation comparison based on complex-valued signals and amplitude scattered signals according to the embodiment of the present invention.

The present invention enables the collection of complex-valued dynamic light scattered signals that contain both amplitude and phase information. However, in the conventional dynamic light scattering detection, the intensity (or amplitude) signal of particle scattering is detected by a single-point detector. In fact, the correlation based on complex vector signals is more accurate than simple correlation based on amplitude signals in statistical calculation of mathematical relativity. For example, for two samples with same magnitude value but different phase values, they are exactly the same only from an amplitude-dependent point of view; however, from a complex correlation point of view, they are in fact not exactly the same due to the different phases. In order to verify this, a method of testing the correlation function of particles with a standard diameter $\Phi 100$ nm as shown in FIG. 3 is used, wherein the correlation function is calculated by respectively using the amplitude-based scattered signal and the complex-based scattered signal. The curve of correlation as a function of time is shown in FIG. 5, wherein can be intuitively seen that the standard deviation obtained from the correlation curve based on the amplitude signal is larger than that obtained from the complex signal. The standard deviation of the former is 0.11 and the standard deviation of the detection curve obtained by the complex signal is 0.06 at the position of the decorrelation period, which fully shows that the complex scattered signal collected by the present invention helps to improve the detection accuracy. In addition, it is worth mentioning that: it can be seen from the drawings that a decorrelation rate of the correlation curve based on the complex numbers is 0.5 times of the amplitude, which is consistent with the theoretical analysis of a Siegert equation.

The present invention can obtain the sampling volumes in different space positions through the detection, and realize the imaging of the spatially resolved particle dynamic features (such as the diffusion coefficient). When the scattered signal is collected, the detecting light beam is focused on a certain point of the sample and the complex scattered signals of all the depth directions are collected in parallel with certain time intervals (13 μs). The collection period of each position depends on the decorrelation period calculated standard particle theory.

Using the scanning mirror 38 of the detection portion of the device of the present invention, the focus position of the detecting light beam is changed, and all scattered signal samples in all the depths are finally collected at different lateral space positions by moving 256 positions laterally.

In order to ensure resolution in the depth direction, a plurality of sampling volumes are obtained by segmenting the spectrum in the spectral dimension in the depth direction. Finally, in a two-dimensional space containing depth and lateral directions, for each space position, a 7×7×4 window (respectively corresponding to the depth, lateral and spectral dimensions, wherein the spectral dimension of 4 indicates segmenting the spectrum into 4 sub-spectrums) is selected to form a sample ensemble (containing a total of 196 independent samples). Thus, the correlation function at each space position is calculated by using the calculation method of ensemble correlation as described above, and the detected time correlation function is fitted according to the exponential distribution by the least square method, for finally obtaining the diffusion coefficient Dr of each space position.

Figure 6:
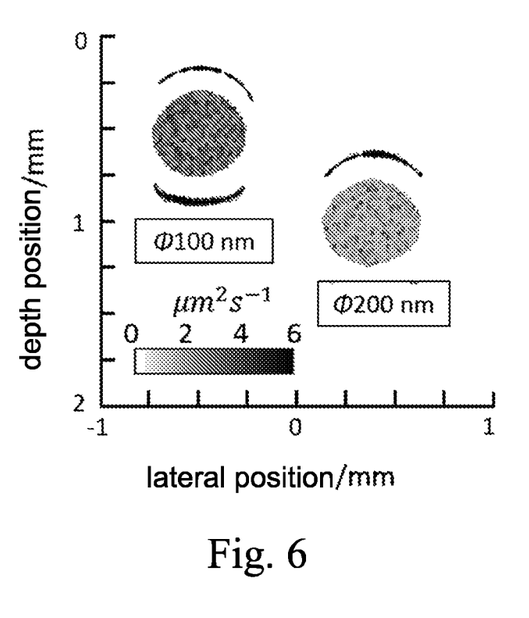
FIG. 6 illustrates characteristics of particle diffusion coefficient according to the embodiment of the present invention.

FIG. 6 shows the imaging of the diffusion coefficient of a particle sample (polystyrene aqueous solution with standard diameters of Φ100 nm and Φ200 nm, and a concentration of 10 vol %) in two-dimensional space using the present invention. The particle solution is injected into a glass tube having an inner diameter of 500 μm. A total of 10 measurements are repeated, and averaged diffusion coefficients are calculated to be 4.66±0.23 μm$^2$/s (shown on the left, Φ100 nm) and 2.14±0.13 μm$^2$/s (shown on the right, Φ200 nm), which are in agreement with the theoretical diffusion coefficients (4.57 μm$^2$/s and 2.28 μm$^2$/s) respectively.

Therefore, the present invention can shorten the period of a single particle detection to several milliseconds to several tens of milliseconds, enabling real-time detection, and obtaining more accurate and reliable correlation characterization. The present invention is capable of determining spatially resolved particle dynamic characteristics with outstanding technical effects.

What is claimed is:

1. A method of ultrafast particle dynamics measurement based on photon ensemble correlation spectroscopy, comprising steps of:
    dispersing a particle sample to be detected;
    establishing a plurality of sampling volumes, and collecting dynamic scattered light signals in parallel; and
    constructing sample ensembles based on scattered signals of the sampling volumes, analyzing time correlations between the sample ensembles, and detecting particle dynamic characteristics;
    wherein establishing the sampling volumes and collecting the dynamic scattered light signals in parallel specifically comprise a step of collecting the dynamic scattered light signals with a low coherence interference method; the low coherence interference is time domain low coherence interferometry that changes an optical path of a reference arm by scanning spectral domain low coherence interferometry for recording spectral interference signals using a spectrometer, or swept-source low coherence interferometry for recording the spectral interference signals by using a broadband low-coherence light as a light source;
    wherein during establishing the sampling volumes and collecting the dynamic scattered light signals in parallel, the sampling volumes are distributed in multiple dimensions that include a spatial dimension, a spectral dimension, an angular dimension, a polarization dimension, and a temporal dimension when being supported by a particle detection speed;
    wherein the temporal dimension comprises a depth space along an optical axis direction, and a lateral space perpendicular to the optical axis direction;
    wherein the spectral dimension is formed by a plurality of detecting light beams of different spectrums in one space region or different space regions; the spectral dimension is specifically formed by a plurality of light sources with different spectrums for illuminating, or segmenting a single spectrum after using a wide-spectrum light source for illuminating, or both;
    wherein the angular dimension is formed by a plurality of detecting light beams incident on a same space region or different space regions from different angles, and then using optical path encoding to segment, or segmenting a transverse modulation spectrum, or detecting with multiple detectors;
    wherein for further establishing the sampling volumes in the temporal dimension, a sample ensemble with more samples is formed at any one of current time points by combining samples in the sampling volumes of subsequent time points and the current time points;
    wherein during establishing the sampling volumes and collecting the dynamic scattered light signals in parallel, the dynamic scattered light signals are amplitude signals, or complex signals comprising both amplitude information and phase information.

2. The method of the ultrafast particle dynamics measurement based on the photon ensemble correlation spectroscopy, as recited in claim 1, wherein dispersing the particle sample to be detected specifically comprises a step of dispersing a liquid particle sample to be detected with a wet method or dispersing a gas particle sample to be detected with a dry method.

3. The method of the ultrafast particle dynamics measurement based on the photon ensemble correlation spectroscopy, as recited in claim 1, further comprising steps of reducing multi-scattered components in the scattered signals and retaining single-scattered components by combining a space gate and a coherence gate technique with low coherence interference.

4. The method of the ultrafast particle dynamics measurement based on the photon ensemble correlation spectroscopy, as recited in claim 1, wherein:
    the depth space along the optical axis direction is formed by the scattered signals in all depth directions obtained in parallel through Fourier domain low coherence interferometry; and
    the lateral space perpendicular to the optical axis direction is formed by illuminating different space regions with a plurality of detecting light beams.

5. The method of the ultrafast particle dynamics measurement based on the photon ensemble correlation spectroscopy, as recited in claim 1, wherein constructing the sample ensembles based on the scattered signals of the sampling volumes, analyzing the time correlations between the sample ensembles, and detecting the particle dynamic characteristics specifically comprise steps of: defining a time point as an initial time point, calculating the time correlations between the sample ensembles of subsequent time points and the initial time point, and detecting the particle dynamic characteristics according to decay characteristics of ensemble correlations over time.

6. The method of the ultrafast particle dynamics measurement based on the photon ensemble correlation spectroscopy, as recited in claim 1, wherein detecting the particle dynamic characteristics specifically comprises a step of: obtaining particle size information through correlation calculation when a viscosity is certain; or obtaining viscosity information through the correlation calculation when a particle size is certain.

7. An apparatus of ultrafast particle dynamics measurement based on photon ensemble correlation spectroscopy, comprising:
- a particle sample dispersing device, for dispersing a particle sample to be detected into a space;
- an optical illuminating and detecting device, for establishing a plurality of sampling volumes, and collecting dynamic scattered light signals in parallel with a low coherence interference method, wherein the low coherence interference further comprises time domain low coherence interferometry that changes an optical path of a reference arm by scanning; spectral domain low coherence interferometry for recording spectral interference signals using a spectrometer; and swept-source low coherence interferometry for recording the spectral interference signals by using a broadband low-coherence light as a light source; and
- at least one processor, for analyzing scattered signals detected;

wherein:
the optical illuminating and detecting device comprises elements selected from a group consisting of:
- an illuminating device using a plurality of light beams to illuminating different lateral space positions perpendicular to an optical axis direction, and a multi-detector device, for establishing the sampling volumes in a space dimension;
- an illuminating device using the light beams to illuminating a same space position or different space positions with different incidence angles, and the multi-detector, for establishing the sampling volumes in an angular dimension;
- a single-beam illuminating device formed by a plurality of sub-beams, wherein the sub-beams have different optical path delays and illuminate the same space position or the different space positions with the different incidence angles, so as to establish the sampling volumes in the angular dimension and detect the sampling volumes in parallel with optical path coding; and
- a multi-beam illuminating device with different spectrums, wherein different light beams illuminates the same space position or the different space positions; which is specifically formed by using a plurality of light sources of the different spectrums for illuminating, or segmenting a single spectrum after using a wide-spectrum light source for illuminating, or both, for establishing the sampling volumes in a spectral dimension;

wherein analyzing the scattered signals detected by the processor further comprises constructing the sampling volumes by segmenting a spectrum, an optical path or a transverse scanning modulation spectrum during analyzing the scattered signals detected;

wherein during establishing the sampling volumes and collecting the dynamic scattered light signals in parallel, the sampling volumes are distributed in multiple dimensions that include a spatial dimension, a spectral dimension, an angular dimension, a polarization dimension, and a temporal dimension when being supported by a particle detection speed;

wherein the temporal dimension comprises a depth space along an optical axis direction, and a lateral space perpendicular to the optical axis direction;

wherein the spectral dimension is formed by a plurality of detecting light beams of different spectrums in one space region or different space regions; the spectral dimension is specifically formed by a plurality of light sources with different spectrums for illuminating, or segmenting a single spectrum after using a wide-spectrum light source for illuminating, or both;

wherein the angular dimension is formed by a plurality of detecting light beams incident on a same space region or different space regions from different angles, and then using optical path encoding to segment, or segmenting a transverse modulation spectrum, or detecting with multiple detectors;

wherein for further establishing the sampling volumes in the temporal dimension, a sample ensemble with more samples is formed at any one of current time points by combining samples in the sampling volumes of subsequent time points and the current time points;

wherein during establishing the sampling volumes and collecting the dynamic scattered light signals in parallel, the dynamic scattered light signals are amplitude signals, or complex signals comprising both amplitude information and phase information.

8. The apparatus of the ultrafast particle dynamics measurement based on the photon ensemble correlation spectroscopy, as recited in claim 7, wherein:
the optical illuminating and detecting device comprises:
a low coherence light source, an interferometer and a detector;
or comprises the low coherence light source, the interferometer and a spectrograph;
or comprises a swept-frequency wide-spectrum light source, the interferometer and the detector.

9. The apparatus of the ultrafast particle dynamics measurement based on the photon ensemble correlation spectroscopy, as recited in claim 7, wherein analyzing the scattered signals detected by the processor further comprises defining a time point as an initial time point, calculating the time correlations between the sample ensembles of subsequent time points and the initial time point, and detecting the particle dynamic characteristics according to decay characteristics of ensemble correlations over time.

* * * * *